United States Patent [19]

Brewer et al.

[11] Patent Number: 4,947,859
[45] Date of Patent: * Aug. 14, 1990

[54] BIO-ACOUSTIC SIGNAL SENSING DEVICE

[75] Inventors: James E. Brewer, Maplewood; Mark W. Kroll, Minnetonka, both of Minn.

[73] Assignee: Cherne Medical, Inc., Edina, Minn.

[*] Notice: The portion of the term of this patent subsequent to Jun. 16, 2004 has been disclaimed.

[21] Appl. No.: 301,796

[22] Filed: Jan. 25, 1989

[51] Int. Cl.$^5$ .............................................. A61B 5/02
[52] U.S. Cl. .................................. 128/715; 128/773; 381/169; 381/187
[58] Field of Search ................... 128/725, 773, 660.01; 381/153–154, 169, 187–188

[56] References Cited

U.S. PATENT DOCUMENTS

| 3,387,149 | 6/1968 | Young | 128/715 X |
| 4,556,066 | 12/1985 | Semrow | |
| 4,672,976 | 6/1987 | Kroll | 128/715 |

OTHER PUBLICATIONS

Balmaseda, M. T., et al., Ohio State University, Ultrasound Therapy: A Comparative Study of Different Coupling Media, 1986.
Shimada, J., et al., U.S. patent application for Bio-Acoustic Transmission Medium, Filing Date: 3/24/89, Ser. No. 07/328,167.

Primary Examiner—Max Hindenburg
Assistant Examiner—John P. Lacyk
Attorney, Agent, or Firm—Anthony G. Eggink; Joel D. Skinner

[57] ABSTRACT

This invention provides a sound sensor apparatus for reception of bio-acoustic signals from the body of a patient and for use with a medical diagnostic device. The apparatus comprises a unitary containment structure of a pliable, adhering material for conforming placement on the patient body surface. A sound sensing transducer is embedded in the containment structure to receive and convert bio-acoustic signals to electrical signals. A cable is communicatively linked to the sound sensing transducer for transmitting the electrical signals to the medical diagnostic device. The composition of the pliable containment structure material is a polymeric mixture substantially acoustically matched to the patient body. The sound sensing transducer is preferably a piezoelectric crystal transducer constructed of a composite material which comprises at least 65 percent by weight lead, at least 20 percent by weight zirconium, and at least 10 percent by weight titanium.

21 Claims, 3 Drawing Sheets

BIO-ACOUSTIC SIGNAL SENSING DEVICE

BACKGROUND OF THE INVENTION

This invention relates to diagnostic devices and, more particularly, to medical sensing devices used to detect energy in the audible range. The device of this invention is particularly useful for the detection of a broad range of frequencies of bio-acoustic signals or sound waves generated by the human body, particularly those by the heart.

Acoustical signals emanating by and from the human body are monitored and analyzed for a variety of purposes such as phono-cardiography. Phono-cardiography involves the detection of acoustical signals produced by the movement of heart muscle, heart valves and resultant blood flow which are transmitted through chest cavity tissues primarily to the chest and back skin surfaces. A sensor is typically placed at a predetermined, precordial location on the patient body surface to receive and transmit these signals.

In the past, a variety of sensors have been proposed or utilized to detect and analyze heart as well as other bio-acoustic signals. These sensor devices range from primarily mechanical devices, such as stethoscopes, to electronic devices, such as microphones and accelerometers. These prior art sensors have various limitations including the distortion and attenuation of sound waves, the necessity for continuous "hands-on" operator manipulation, and the inability to simultaneously detect high and low frequency signals.

A major problem with existing sensors is that they do not "couple" well to the body surface due to the impedance difference between the soft body tissues and the adjacent air. This impedance mismatch can result in acoustical energy losses exceeding 99 percent. Thus, only a small amount of an acoustical signal is transmitted from the body by present sensors or transducers.

Attempts in the prior art to deal with the coupling problem include disposing a hydrophone in a liquid medium, such as a gel or water. The hydrophone senses sounds in the liquid environment, as opposed to the gaseous fluid environment of a microphone. A problem with such a device, however, is the required use of a flexible membrane or diaphragm which permits the medium to closely contact the body surface. These and other prior art devices usually also require gel to be applied over the patient's skin for interfacing the membrane or diaphragm. This requirement is messy, time consuming and results in coupling losses between the gel and diaphragm boundary and between the diaphragm and transducer due to the interior fluid medium. Coupling losses of approximately 10 percent can result from sound wave transmittance across such flexible diaphragms. Further, hydrophonic fluids may chemically react with or degrade the diaphragm structure of the sensor devices.

Prior art sensors utilizing fluid mediums further have difficulty with suspended gas bubbles in the hydrophonic media which result in high sound wave attenuation or energy loss. These attenuation losses are primarily due to viscous forces and heat conduction losses associated with the compression and expansion of small gas bubbles caused by the traveling sound wave. The resultant gas bubbles in the transmission medium also cause sound wave scattering which further results in sound wave energy loss. The presence of gas bubbles affects the physical characteristics of the medium by altering its density and compressibility which effects sound wave speed and which can result in considerable acoustic energy reflection and refraction losses.

Despite the need for a bio-acoustic sensing device, particularly which overcomes the limitations of the prior art in the medical diagnostic art, and which provides reliable reception of sound waves, particularly in the sub-kilohertz (KHz) range, none insofar as is known has been proposed or developed.

Accordingly, it is an object of the present invention to overcome these prior art limitations and to provide a bio-acoustic signal sensing device that is effective and economical to make and use, that detects a broad range of heart sound frequencies, particularly low frequency sounds, and that minimizes heart sound wave distortion and attenuation.

SUMMARY OF THE INVENTION

The sound sensor apparatus of the present invention is for reception of bio-acoustic signals from the body of a patient and being for use with a medical diagnostic device. The apparatus comprises a compact and unitary containment means constructed entirely of a flexible, pliable material. The containment means is for conforming placement to contact the body surface and which is molded of a homogeneous compound that is substantially acoustically matched to the patient body. Sound sensing means is embedded in the containment means and which receives and converts the bio-acoustic signals to electrical signals. Connection means is communicatively linked to the sound sensing means for transmitting electrical signals to the medical diagnostic device.

The sound sensing means is preferably a piezoelectric crystal transducer constructed of a composite material. The composite material preferably comprises at least 65 percent by weight lead, at least 20 percent by weight zirconium, and at least 10 percent by weight titanium, or alternatively polyvinylidene fluoride. In another embodiment of the sound sensor apparatus, the transducer comprises a fiber-optic coupler having an input optical fiber inputting a carrier light signal, coupling means connected to the first optical fiber, and a pair of output optical fibers communicatively connected to the input optical fiber at the coupling means, whereby the bio-acoustical signals impact the coupling means to modulate transmission of the carrier light signal to the output optical fibers.

The containment means is constructed of a polymeric compound comprising a copolymer mixture in an amount of at least 5 percent by weight and having styrene end segments and elastomeric mid-segments linking the styrene end segments. The compound further comprises a mineral oil in an amount of at least 45 percent by weight and an adhesive agent in an amount of up to 30 percent by weight.

The apparatus of this invention is usable directly on the patient body. The flexible and pliable containment media easily conforms to the contours of the body surface to enhance heart sound signal transfer and resolution by minimizing gaps between the body surface and the embedded sound sensing transducer. Further, the properties of the containment media minimize sound wave loss and distortion by reducing the acoustical parameter differences with respect to body tissues.

These and other benefits of this invention will become clear from the following description by reference to the drawings.

DESCRIPTION OF THE PREFERRED EMBODIMENT

Figure 1:
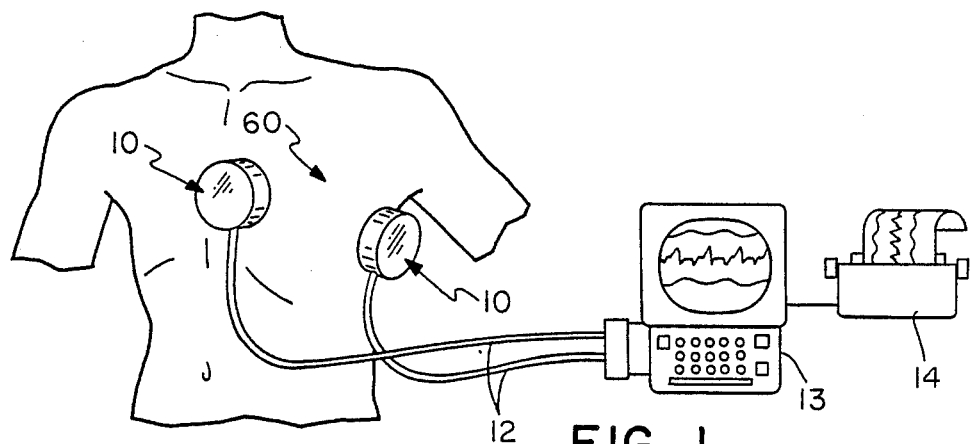
FIG. 1 shows a pair of bio-acoustic signal sensing devices of the present invention placed in an operative orientation on a patient and further being connected to a medical diagnostic apparatus.

FIG. 1 shows a pair of sound sensing apparatus or devices 10 placed in an operative position at predetermined locations on a patient body. In use, a physician or other medical personnel determines the appropriate positioning locations on the patient, for example, on the precordial or thoracic region 60 depending upon particular characteristics of the patient and the nature of the diagnostic test to be performed. Although two devices 10 are shown being used, a single device or additional devices may also be used consistent with this invention.

The sound sensing device 10 is used to receive bio-acoustic signals transmitted from the patient and to convert the acoustical signals to electrical signals. The device 10 is communicatively connected via a cable or cable set 12 to a medical diagnostic device 13 which is used to analyze these converted bio-acoustic signals, such as heart sound waves. As further shown in FIG. 1, the medical diagnostic device 13 may be communicatively linked to a printer 14 for generating a printed copy of the diagnostic results. The device 10 is generally thin and flat so that it will easily remain in direct contact and in position on and with the body surface during use. The devices 10 are shown to be self-adhering to the body 60, alternatively however, the devices may be held in place by other securement means such as flexible straps having end connectors or the like. Although it is not required under the present invention, prior to placement of the device 10 on the patient body surface 60, an acoustic coupling gel, such as Aquasonic 100 TM, produced by Parker Labs, or Lectro-Sonic TM, produced by Burdick, may be applied to the placement position. As described further below, the structure of the sound sensing device 10 of this invention is economical in manufacture and thus, may be disposable after use.

Figure 2:
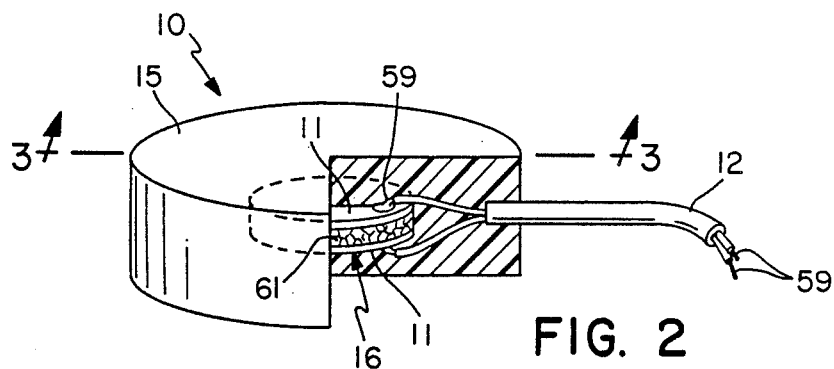
FIG. 2 is a perspective view, partially in cross-section, of the bio-acoustic signal sensing device.
Figure 3:
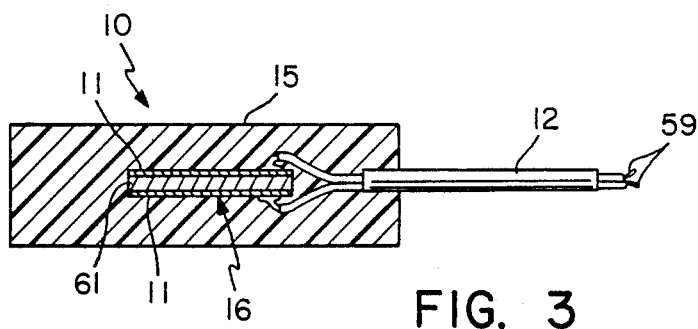
FIG. 3 is a cross-sectional view of the device of FIG. 2, taken on line 3–3.

Referring to FIGS. 2 and 3, the signal sensing device or sensor 10 generally comprises a compact containment media or structure 15 composed entirely of a flexible and pliable material, a sound sensing transducer 16 which is embedded in the containment media 15, and the connection cable 12 which is communicatively linked to the transducer 16 and to the medical diagnostic device 13. The connection cable 12 is of a type known in the medical field. It preferably has a pair of inner conductors 59 which are connected to the sound sensing transducer 16. A non-conductive insulation surrounds the conductors 59.

The containment media or structure 15, as shown, has a compact, molded circular or disk shaped configuration with a diameter of approximately 2 inches (5 cm.) and a thickness of approximately 0.5 inches (1 cm.). These dimensions are particularly desirable for reception of low frequency heart sound signals. Alternative configurations such as an oval, square or rectangular shape are also usable consistent with the invention. The flexible material of the containment media 15 easily conforms to the contours of the patient body surface. This conforming structural configuration and its cooperation with the embedded sound sensing transducer 16 enhances heart sound signal transfer and resolution by minimizing gaps between the body surface and the device 10. Further, the flexible structure is preferably of a composition which reduces sound wave loss and distortion by minimizing acoustical parameter differences between the device 10 and the patient body surface. The containment structure 15, therefore, is preferably constructed of a thermoplastic rubber polymer compound which has pliable or flexible physical properties. Importantly, the compound of the containment structure 15 is acoustically matched, or in other words, has acoustical properties which are substantially equivalent to the tissues of the human body. The compound has a density times sound transmittance velocity product which preferably ranges from $1.5 \times 10^4$ to $1.5 \times 10^6$ gm/cm² sec.

The energy transmission between two acoustical media can be represented by the equation $\alpha_+ = 4p_1c_1p_2c_2/(p_1c_1 + p_2c_2)^2$ where p is the density and c is the sound velocity in each medium. This equation can be rewritten as $$\alpha_+ = 1 - \left(\frac{p_2c_2 - p_1c_1}{p_2c_2 + p_1c_1}\right)^2.$$

Thus, to achieve 100% transmission, $p_2c_2 = p_1c_1$ or the product of the density and sound velocity must be equal for the two different media. For example, water has $p=1$ gm/cm³ and $c=1.45 \times 10^5$ cm/sec. Air has $p=1.29 \times 10^{-3}$ gm/cm³ and $c=3.3 \times 10^4$ cm/sec. Therefore, $p_1c_1 = 1.45 \times 10^5$ gm/cm²/sec. and $p_2c_2 = 42.57$ gm/cm² sec. where media 1 and 2 are water and air, respectively. This yields $\alpha_+ = 0.0012$ or about 0.12% of acoustical energy is transmitted between water and air. Since mammalian bodies are acoustically similar to water, this same loss is generally found when sound travels from the human body to the adjacent air.

The containment media 15 compound, therefore, preferably has a styrene-elastomer-styrene polymeric structure which is formulated of at least 5 percent polymer by weight and at least 45 percent mineral oil by weight. The mineral oil forms physical cross links between the individual polymer molecules. In its preferred embodiment, the compound additionally comprises an adhesive agent in an amount of not more than 30 percent by weight and an anti-oxidizer in an amount of not more than 5 percent by weight, for example, sodium E.D.T.A.

The preferred embodiment of the compound comprises 10–30 percent by weight polymer, 45–75 percent by weight mineral oil, and between 5 and 20 percent adhesive agent. The mineral oil is preferably a food grade, medium viscosity oil (type 7NF) as known in the art. The polymer molecule is comprised of styrene end segments or domains, which are linked by an elastomer or rubber phase. The styrene end segments are preferably polystyrene. The elastomer mid-segment is selected from the group consisting of polyisoprene, polybutadiene and poly(ethylene-butylene). Such styrene-butadiene-styrene (S-B-S), styrene-isoprene-styrene (S-I-S), and styrene-ethylene/butylene-styrene (S-E-B-S) copolymers are produced, for example, by Shell Chemical under the trademark Kraton TM. Preferably, grade "D" or "G" Kraton copolymers are utilized. Such copolymers have an average molecular weight of approximately 425,000. Preferably, the adhesive agent is a pressure sensitive adhesive such as Eastobond TM or polyisobutylene. Tackfiers such as Cumar R-16 TM, Piccotex 100 TM, and Pentalyn H TM are also usable, consistent with the teachings of the invention.

The compounds described provide unitary, homogeneous containment structures of varying degrees of pliability and adhesiveness. Generally, as the ratio of mineral oil to copolymer in the compound increases, flexibility increases and adhesiveness decreases. Although particular containment structure compounds are provided herein, additional compounds may be formulated, having the pliable, homogeneous and acoustic transmission characteristics described, to practice the teachings of this invention.

Figure 4:
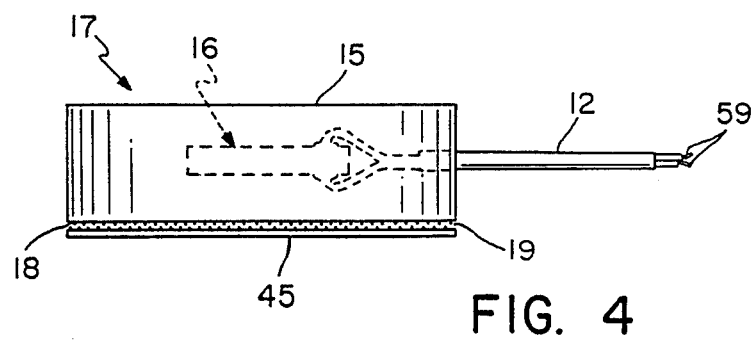
FIG. 4 is a lateral schematic view of another embodiment of the bio-acoustic signal sensing device.

The containment media 15 described above preferably has adhesive properties so that the device 10 conformingly adheres to the patient body without additional securement structures or a separate adhesive layer. Referring to FIG. 4, another embodiment of the bio-acoustic signal sensing device 17 is shown wherein the containment media 15 has a patient contact surface 18 which is coated with an adhesive 19, as known in the art, for conforming adherence to the patient.

The sound sensing transducer 16 is preferably a thin crystal transducer constructed of a composite material. As shown, the transducer 16 has a circular or disk shape, for example, with a diameter of approximately 1 inch (2.5 cm.) and a thickness of approximately 0.05 inches (1 mm.). The crystal 61 exhibits the piezoelectric effect whereby transmitted sound waves subject the crystal 61 to a mechanical stress which sets up an electrical polarization and causes the faces of the crystal 61 to become electrically charged. The polarity of the charges reverses as crystal compression changes to crystal tension. As known, an approximately linear relationship exists between crystal 61 deformation and electric field strength and the change in electric field strength along the axes in the crystal 61 can be defined by known equations relating to the incremental stress and the piezoelectric strain constant. The transducer 16 has conductive layers 11 on its top and bottom surfaces which conduct electrical signals produced via the piezoelectric activity of the crystal 61. Individual insulated lead wires 59 are communicatively connected to the conductive layers 11 and extend to form the cable 12. The composite material of the crystal 61 preferably comprises a mixture of at least 65 percent by weight lead, at least 20 percent by weight zirconium, and at least 10 percent by weight titanium. Such a crystal 61 composition provides a relatively high output and good frequency response. Alternatively, the crystal 61 may be constructed of polymeric polyvinylidene fluoride to provide increased flexibility for cooperation with the containment media 15.

Figure 5:
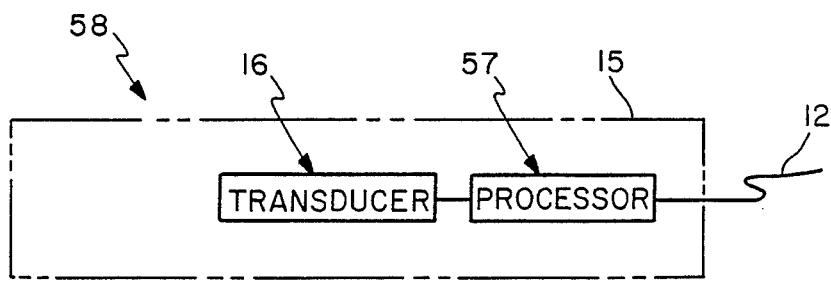
FIG. 5 is a schematic diagram of an alternative embodiment of the bio-acoustic signal sensing device.

Referring to FIG. 5, in an alternative embodiment of the bio-acoustic signal sensing device 58, a processor 57 is shown to be connected directly to the sound sensing transducer 16 within the containment media 15. In this embodiment of the sensor 58, the received acoustic signals are processed prior to transmission to the medical diagnostic device 13. Such processing may include signal amplification, signal enhancement, signal filtering, current limitation or the like. The signal processor 57 is communicatively linked to the connection cable 12.

Figure 6:
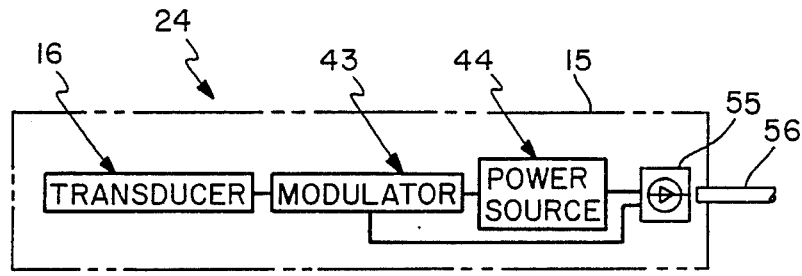
FIG. 6 is a schematic diagram of another embodiment of the bio-acoustic signal sensing device.

FIG. 6 shows another embodiment of the bio-acoustic signal sensing device 24 wherein the sound sensing transducer 16 is communicatively connected to a phototransmitter 55 and an optical fiber link 56. Electrical signals produced by the transducer 16 are provided to a modulator 43, and linked to the phototransmitter 55 which converts them to optical signals. The phototransmitter 55 is further connected to a battery power source 44. The phototransmitter 55 shown in preferably a laser diode, such as an ML 5101 or ML 5401, manufactured by Mitsubishi Electronics America, Inc., Sunnyvale, CA. The optical signals are then transmitted to the medical diagnostic device 13 by the optical fiber 56. A photo detector (not shown) is connected to the optical fiber 56 to convert the transmitted optical signals into electrical signals. The fiber optic link 56 of this low power embodiment provides a patient safety factor due to the electrical isolation of the sensor 24 from the medical diagnostic device 13. Additional fiber optic embodiments of the present invention are also apparent from the teachings of the U.S. Patent Application of Kroll et al. for an Optical Fiber Transmissive Signal Modulation System, Ser. No. 060,741, which is hereby incorporated by reference.

Figure 7:
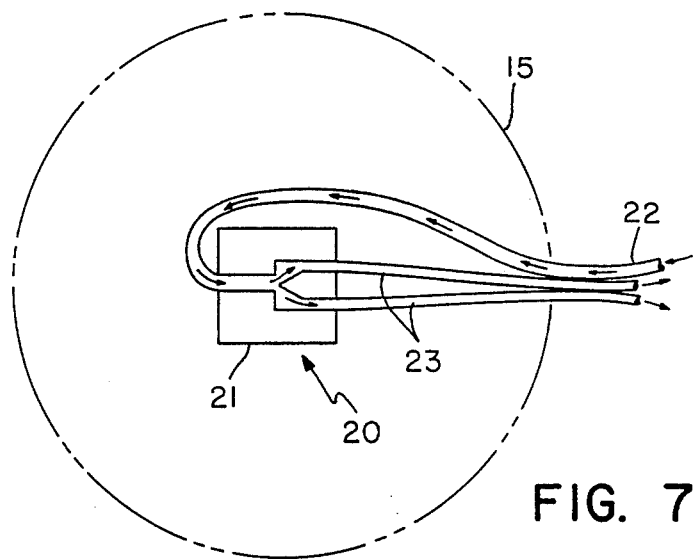
FIG. 7 is a top schematic diagram of an embodiment of the sound sensing transducer of the device.
Figure 8:
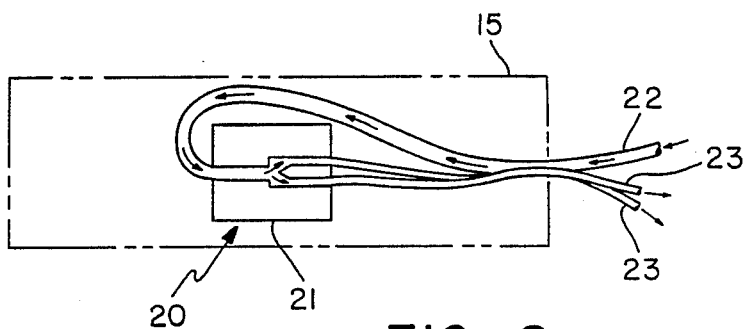
FIG. 8 is a lateral schematic diagram of the transducer shown in FIG. 7.

FIGS. 7 and 8 show an alternative embodiment of the sound sensing transducer 20. The transducer 20 comprises an optical fiber coupler 21 for reception of acoustic signals and for connection of a plurality of optical fibers. The optical fibers are preferably high power, plastic optical fibers, for example, such as those manufactured by Ensign-Bickford Industries, Inc., Simsbury, CT. A first or input optical fiber 22 inputs a carrier optical signal to the optical coupler 21. A pair of output optical fibers 23 are communicatively connected to the input optical fiber 22 by the optical coupler 21 in a generally "Y" shaped configuration. Thus, the carrier optical signal is transmitted from the input optical fiber 22 and split to the pair of output optical fibers 23. In the absence of acoustical signals impacting the optical coupler 21, the splitting ratio of light transmitted to the respective output optical fibers 23 is substantially constant. However, acoustic signals impacting the coupler 21 lodulate transmission of the carrier signal and alter or vary the splitting ratio to the pair of output optical fibers 23. The modulation of the splitting ratio is detected by a pair of photodetectors (not shown), disposed at the ends of the output optical fibers 23, and which produce electrical signals as a function of the received optical energy. This zero power embodiment of the sound sensing transducer 20 also provides a patient safety factor due to the electrical isolation of the transducer 20 from the medical diagnostic device 13.

Figure 9:
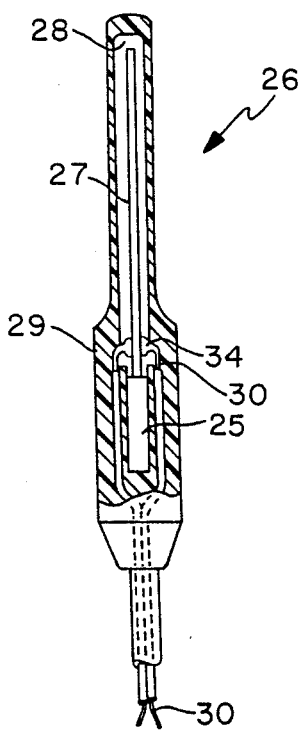
FIG. 9 is a cross-sectional view of an alternative embodiment of the sound sensing transducer.

FIG. 9 shows another embodiment of the sound sensing transducer and which comprises a hydrophone structure 26. The hydrophone 26 is generally centrally placed and embedded within the containment media 15, and produces electrical signals in response to transmitted heart sound waves in the frequency range of 10 to 2,000 Hz. The hydrophone structure 26 is comprised of a cantilever beam crystal 27, a current distribution system 30, a hydrophone cavity 28 and an exterior insulating layer 29. The beam crystal 27 is an elongated, thin, and flexible cantilever beam crystal. Contacts 34 are disposed at opposing sides of the crystal 27 near its supporting base or mounting end 25. The crystal 27 is vibratingly sensitive to sound pressure variations and a proportional electric current is produced by its vibration. The crystal 27 is located within the hydrophone cavity 28 to permit its vibration.

Figure 10:
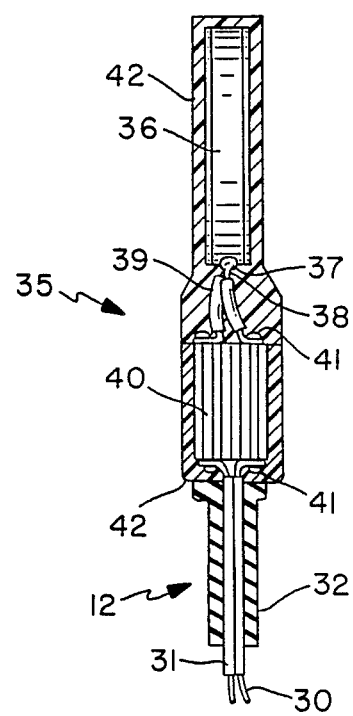
FIG. 10 is a cross-sectional view of another embodiment of the sound sensing transducer used in the sensing device of this invention.
Figure 11:
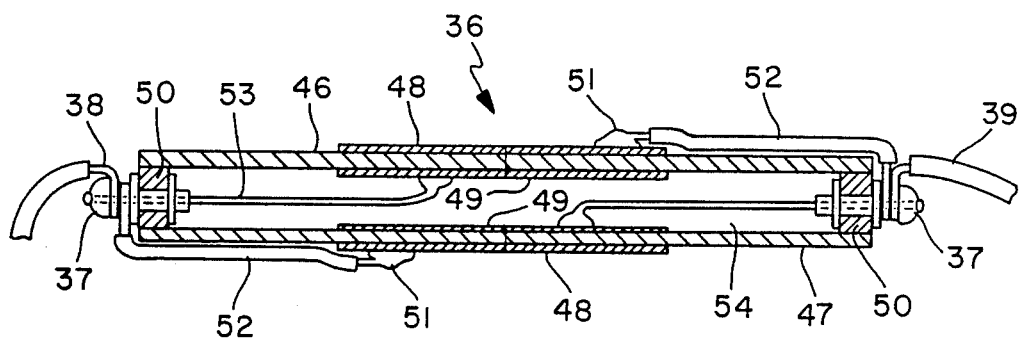
FIG. 11 is a cross-sectional view further showing the crystal plate structure of the transducer shown in FIG. 10.

FIGS. 10 and 11 show an alternative hydrophone embodiment 35, for example, as manufactured by Mark Products, Inc. of Houston, Tex. The hydrophone 35 is shown to be comprised of a circular plate transducer 36, transducer insulation 42, a transformer 40, low voltage lead wires 38, and lead wires 30. The transducer 36 converts input non-electrical bio-acoustic or heart sound waves into output electrical signal parameters. The transducer 36 is communicatively connected to a transformer 40 by the low voltage lead wires 38 (approximately 30 gauge). The low voltage lead wires 38 have an insulation layer 39 and are attached to contacts 37 of the transducer 36. Both low voltage lead wires 38 are shown embedded in transducer insulation 42. The transformer 40 is of a design known in the art which converts the output electrical signal of the transducer 36 into an electrical signal of the same frequency and at an increased alternating voltage. As shown, the current distribution system or lead wires 30 are connected to contacts 41 of transformer 40 which conduct the transformed electrical signal to the heart sound analyzing apparatus 13. Lead wires 30 have a non-conductive inner insulator 31 and a non-conductive outer insulator 32 which collectively form the cable structure 12.

FIG. 11 further shows the circular plate transducer 36 comprising a first plate 46, a second plate 47 and a side wall 50. The first plate 46 and the second plate 47 are respectively bonded to the top and bottom of the side wall 50. The spacially removed plates 46 and 47 form a transducer void area 54 and each serves as a connecting base, respectively, for the piezoelectric outer crystal member 48 and inner crystal member 49 which are likewise spacially separated. The first plate 46, second plate 47 and side wall 50 are preferably composed of a metallic substance suitable for mounting crystals.

The electrical signal produced by crystal members 48 and 49 in response to transmitted sound waves is distributed to the remaining hydrophone 35 conductive elements via outer crystal lead wires 51 and inner crystal lead wires 53 which are disposed in the transducer void area 54. Each wire 51 and 53 is connected to the transducer contacts 37, to which the low voltage lead wires 38 are also attached. Outer crystal lead wires 51 are shown substantially sheathed in insulation 52.

Although particular sound sensing transducer structures are shown and described, other such structures may also be utilized in the sensors of this invention. The criteria for determining suitable transducer structure and function is their adaptability for containment in the media and their means for receiving and transmitting the bio-acoustic waves and corresponding electrical output signals as discussed above. Particularly of importance in this invention, as discussed, is the structural arrangement and cooperation of the transducer embedded within the flexible and pliable containment structure for adhesively conforming to the patient body to detect bio-acoustic signals, particularly heart sounds in the sub KHz range.

The acoustical chemical compositions used in this invention are relatively inexpensive. Additionally, these compositions can be easily molded around the transducer embodiments discussed above. Thus, by molding these compositions about a desired transducer embodiment previously fixed in a mold structure, an economical bio-acoustic signal sensing device can be manufactured to yield a disposable sensor structure. If desired, however, the unitary containment media compositions described are chemically stable to permit sanitizing procedures for repeated sensor use.

As many changes are possible to the embodiments of this invention utilizing the teachings thereof, the descriptions above should be interpreted in the illustrative and not in the limited sense.

That which is claimed is:

1. A sound sensor apparatus for reception of bio-acoustic signals from the body of a patient and being for use with a medical diagnostic device, comprising:
   a. a unitary and flexible containment structure consisting entirely of a pliable, homogeneous polymeric material which is substantially acoustically matched to the human body, and being for conforming placement to contact the patient body surface;
   b. sound sensing means embedded and enclosed within said containment structure, said sound sensing means being constructed and arranged to receive and convert bio-acoustic signals to electrical signals; and
   c. connection means communicatively linked to said sound sensing means for transmitting said electrical signals to the medical diagnostic device.

2. The sound sensor apparatus of claim 1, wherein said sound sensing means comprises a compact, low power transducer means for reception and conversion of bio-acoustic signals to said electrical signals as a function of the received acoustic signals.

3. The sound sensor apparatus of claim 2, wherein said transducer means is a piezoelectric transducer.

4. The sound sensor apparatus of claim 3, wherein said piezoelectric transducer has a crystal which is constructed of a composite material and disposed between two layers of a conductive material.

5. The sound sensor apparatus of claim 4, wherein said composite material contains a mixture of lead, zirconium and titanium.

6. The sound sensor apparatus of claim 5, wherein said mixture comprises at least 65 percent by weight lead, at least 20 percent by weight zirconium, and at least 10 percent by weight titanium.

7. The sound sensor apparatus of claim 4, wherein said composite material is polyvinylidene fluoride.

8. The sound sensor apparatus of claim 2, wherein said transducer means comprises a fiber-optic coupler having an input optical fiber inputting a carrier light signal, coupling means connected to said first optical fiber, and a pair of output optical fibers communicatively connected to said input optical fiber at said coupling means, whereby bio-acoustic signals impacting said coupling means modulates transmission of said carrier light signal to said output optical fibers.

9. The sound sensor apparatus of claim 1, wherein said containment structure is of a compound which is substantially acoustically matched to human body tissues.

10. The sound sensor apparatus of claim 9, wherein said containment structure compound has a density times sound velocity product ranging from $1.5 \times 10^4$ to $1.5 \times 10^6$ gm/cm$^2$ sec.

11. The sound sensor apparatus of claim 1, wherein said containment structure is of a polymeric compound comprising:
 a. a copolymeric mixture in an amount of at least 5 percent by weight, said copolymer mixture having styrene end segments and elastomeric mid-segments linking said styrene end segments;
 b. a mineral oil in an amount of at least 45 percent by weight; and
 c. an agent for increasing the adhesiveness of the compound provided in an amount of up to 30 percent by weight.

12. The acoustic transmission compound of claim 11, wherein said styrene end segments consist of polystyrene, said elastomeric mid-segments are selected from the group of polymers consisting of polyisoprene, polybutadiene, and poly(ethylene-butylene) and said adhesive agent is a pressure sensitive adhesive.

13. The compound of claim 11, additionally comprising an antioxidant.

14. The compound of claim 11, wherein said copolymeric mixture is in an amount of from 10 to 30 percent by weight, said mineral oil is in an amount of from 45 to 75 percent by weight, and said adhesive agent is in an amount of from 5 to 20 percent by weight.

15. The sound sensor apparatus of claim 11, wherein said compound has adhesive properties for adherence to the body of a patient.

16. The sound sensor apparatus of claim 1, wherein said containment structure has a patient contact surface and wherein an adhesive is applied to said patient contact surface for conforming adherence to the body.

17. The sound sensor apparatus of claim 1, further comprising means to convert electrical signals from said sound sensing means to optical signals, and wherein said connection means is an optical fiber communicatively connected to said means to convert.

18. The sound sensor apparatus of claim 1, further comprising signal processing means connected to said sound sensing means.

19. A sound sensor apparatus for reception of bio-acoustic signals from the body of a patient and for use with a medical diagnostic device, comprising:
 a. a flexible pliable, unitary and homogeneous containment means constructed of a material having a density-sound velocity product between $1.5 \times 10^4$ and $1.5 \times 10^6$ gm/cm$^2$ sec., said containment means being for conforming placement onto the patient body surface;
 b. a compact transducer means for reception and conversion of bio-acoustic signals to electrical signals, said transducer means being embedded in said containment means; and
 c. connection means communicatively linked to said transducer means for transmitting said electrical signals to the medical diagnostic device.

20. A compact sound sensor apparatus for reception of bio-acoustic signals from the body of a patient and for use with a medical diagnostic device, comprising:
 a. a flexible and pliable containment means for placement on the patient body surface, said containment means being molded of a unitary structure having a density-sound velocity product of from $1.5 \times 10^4$ to $1.5 \times 10^6$ gm/cm$^2$ sec., said structure being a polymeric cross-linked styrene-elastomer-styrene composition;
 b. a low power transducer means embedded in said molded structure and being constructed and arranged to receive and convert bio-acoustic signals to electrical signals; and
 c. connection means communicatively linked to said transducer means for transmitting said electrical signals to the medical diagnostic device.

21. A sound sensor apparatus for reception of bio-acoustic signals from the body of a patient and being for use with a medical diagnostic device, comprising:
 a. a unitary and flexible containment structure of a pliable, homogeneous material, and being for conforming placement to contact the patient body surface;
 b. sound sensing means embedded in said containment structure, said sound sensing means being constructed and arranged to receive and convert bio-acoustic signals to electrical signals;
 c. means to convert electrical signals from said sound sensing device to optical signals; and
 d. an optical fiber, communicatively linked to said conversion means, for transmitting said optical signals to the medical diagnostic device.

* * * * *